United States Patent [19]

Segall et al.

[11] Patent Number: 4,761,427

[45] Date of Patent: Aug. 2, 1988

[54] LIQUID ANTIMICROBIAL COMPOSITION

[75] Inventors: Jeane Segall; Leonard M. Shorr, both of Haifa, Israel

[73] Assignee: Bromine Compounds Ltd., Beer-Sheva, Israel

[21] Appl. No.: 805,792

[22] Filed: Dec. 6, 1985

Related U.S. Application Data

[63] Continuation-in-part of Ser. No. 650,551, Sep. 12, 1984, abandoned, which is a continuation of Ser. No. 442,189, Nov. 16, 1982, abandoned.

[30] Foreign Application Priority Data

Feb. 28, 1982 [IL] Israel ........................................ 65126

[51] Int. Cl.$^4$ ............................................ A01N 37/34
[52] U.S. Cl. .................................... 514/528; 162/161; 210/764
[58] Field of Search ................. 514/528; 210/62, 64; 162/161

[56] References Cited

U.S. PATENT DOCUMENTS

| | | | |
|---|---|---|---|
| 2,419,888 | 4/1947 | Nolan et al. | 514/528 |
| 3,493,658 | 2/1970 | Schmidt et al. | 514/528 |
| 3,557,184 | 1/1971 | Toepfl et al. | 544/163 |
| 3,733,332 | 5/1973 | Toepfl | 546/245 |
| 4,022,605 | 5/1977 | Konya et al. | 71/67 |
| 4,163,795 | 8/1979 | Burk | 514/528 |
| 4,163,796 | 8/1979 | Burk | 514/528 |

FOREIGN PATENT DOCUMENTS

1321323 6/1973 United Kingdom .

Primary Examiner—Allen J. Robinson
Attorney, Agent, or Firm—Browdy and Neimark

[57] ABSTRACT

Aqueous antimicrobial compositions in which dibromonitrilopropionamide is the active ingredient contain from 1% to the solubility limit of dibromonitrilopropionamide, from 5% to the solubility limit of water and a balance of up to 100% of a propylene glycol (all percentages being by weight). Tests on stability carried out on the aqueous antimicrobial compositions show that the rates of decomposition are completely satisfactory compared with the rates of decomposition of known compositions.

10 Claims, No Drawings

4,761,427

LIQUID ANTIMICROBIAL COMPOSITION

CROSS REFERENCE TO RELATED APPPLICATION

The present application is a continuation-in-part of application Ser. No. 650,551, filed Sept. 12, 1984, now abandoned, which is a continuation of Ser. No. 442,189, filed Nov. 16, 1982, now abandoned, the entire contents of which are hereby incorporated by reference.

FIELD OF THE INVENTION

The present invention relates to antimicrobial compositions and methods of use. More particularly, the present invention relates to antimicrobial compositions and methods of using same in which the compositions contain halogenated cyanoamide as active ingredient.

BACKGROUND OF THE INVENTION

The use of halocyanoacetamides in various compositions as antimicrobials is well known for various applications as described in U.S. Pat. No. 2,419,888; U.S. Pat. No. 3,493,658 and Belgian Patent No. 668,336. Certain of the compounds are useful as slimicides in aqueous systems such as paper pulp and others are useful in the finishing of textiles.

In the preparation, storage, shipment and use of antimicrobial agents it is often desirable to employ the agents in the form of liquid concentrate compositions. The properties which are sought for such concentrates include stability over extended periods under a variety of conditions of temperature, humidity, freeze-thaw cycles and the like, compatibility with conventional container materials, and ready diluability in the formulation of treating compositions. A liquid concentrate composition containing a halocyanoacetamide and having the above properties has been long sought.

According to U.K. Pat. No. 1,321,323, there are provided liquid antimicrobial compositions comprising from 1 to 60% halocyanoacetamide in an organic liquid selected from straight chain polyalkylene glycols of the ethylene or trimethylene series and low alkyl ethers thereof, the organic liquid having an average molecular weight of from 135 to 600. This patent discloses that many common organic solvents, such as diethyl ether, ethylene glycol, polypropylene glycol, etc, are unsuitable for use with bromocyanoacetamide, since the concentration of the latter decreases rapidly in relatively short periods of time due to decomposition. Such decomposition is often accompanied by the appearance of colored decomposition products and tarry residues, and the formation of solids. The same patent also discloses that halocyanoacetamide compounds, while active in the presence of water, possess insufficient storage stability in aqueous concentrate solutions to permit convenient storage and shipping of aqueous concentrates. Substantial losses in active ingredient concentration and antimicrobial potency often occur after such storage.

The British patent contains a specific example showing that when bromocyanoacetamide is stored in a concentrated solution in polypropylene glycol 400, a yellow color rapidly develops turning to a brown discoloration with formation of a precipitate after eight days of accelerated aging. Furthermore, more than 80% of the initial bromocyanoacetamide concentrate is lost. Another example specifically shows that using the preferred solvent, polyethylene glycol 200, the addition of up to 16 parts by weight of water does not change the results which are obtained in the absence of water, but more water destroys the effectiveness of the solvent and leads to a loss of bromocyanoacetamide concentration.

In order to reduce the adverse impact of water upon said composition, the prior art describes a series of stabilizers, such as azines, quaternary ammonium or phosphonium compounds, etc. (see for example Israeli patent application No. 55,863 and U.S. Pat. No. 4,163,795).

U.S. Pat. No. 4,022,605 to Konya et al discloses a composition including halocyanoacetamide in a solvent with 0.01–10 weight % of a stabilizer. The solvent may be a polyol, such as polyethylene glycol 200. The stabilizer may be 1,2-propanediol or 1,3-propane-diol. There is no disclosure in Konya of the use of a propane-diol as a solvent or the presence of water for any purpose.

SUMMARY OF THE INVENTION

Accordingly, it is an object of the present invention to solve the problems of the prior art.

It is another object of the present invention to provide a liquid concentrate of an antimicrobial composition containing a halogenated cyanoacetamide as active ingredient which is stable over extended periods, compatible with conventional container materials and dilutable in the formulation of anti-microbial compositions.

It is yet another object of the present invention to provide such a composition in which the halogenated cyanoacetamide is dibromonitrilopropionamide (hereafter referred to as DBNPA).

It is yet another object of the present invention to provide methods of inhibiting microbial growth by using the compositions of the present invention.

These and other objects of the present invention will be better understood from a reading of the following description of the invention.

DETAILED DESCRIPTION OF PREFERRED EMBODIMENTS

It has unexpectedly been found that although polypropylene glycol is an unsuitable formulation solvent for DBNPA and although aqueous solution of DBNPA is unstable and dilution with water of polyethylene glycol solutions of DBNPA contributes to instability, when antimicrobial compositions containing DBNPA are prepared in a solvent consisting of propylene glycols (as hereafter defined) in the presence of water, said compositions are stable.

Thus, the present invention consists of antimicrobial compositions comprising a solution of dibromonitrilopropionamide in aqueous propylene glycols, the weight ratios between said components being from 1% to its solubility limit of dibromonitrilopropionamide, from 5% to its solubility limit of water (preferably 5–30% water), the balance being propylene glycols. The term "propylene glycols", as utilized in the present specification and claims, means monopropylene glycol, dipropylene glycol, polypropylene glycol, preferably an average molecular weight of about 425, or any mixture thereof. The compositions according to the present invention retain high active ingredient concentration and accordingly high antimicrobial activity for long periods of time. Thus, for instance it has been found that DBNPA (20 parts) with dipropylene glycol (80 parts), in the absence of water, will decompose at a rate of 2.3% per day, in an accelerated test carried out at 50° C. Under the same conditions of testing, in a composition containing 20 parts DBNPA, 30 parts water and 50 parts dipropylene glycol, the decomposition of the DBNPA was only 0.12% per day. Thus, by the addition of water to the solution of DBNPA in dipropylene glycol an almost twentyfold increase in stability is observed. This is completely unexpected from the prior art teachings on this subject. Considering the relatively high temperature under which this accelerated test was conducted, the latter decomposition rate is relatively low and compares very favorably with the decomposition rates of known compositions described in the prior art.

Propylene glycols, and most particularly dipropylene glycol, are well known commercial reagents which are available in bulk quantities and are relatively inexpensive compared with other organic solvents used for this purpose.

The maximum amount of DBNPA in the compositions of the present invention is not critical as long as it is soluble in the propylene glycol-water solvent mixture. The solubility limit of DBNPA in any such mixture is readily determinable by anyone of ordinary skill in the art without undue experimentation. For example, simple testing shows that the solubility limit of DBNPA in dipropylene glycol at 25° C. is about 45% by weight. While the maximum amount of water is also not critical, it is preferable that the weight percent of propylene glycol be greater than that of the water in the composition. Preferred compositions are 1–30% by weight (preferably 5–30% by weight) DBNPA and 5–30% water with the balance propylene glycol.

In the following Table 1 are presented the results concerning the stability of DBNPA in aqueous solutions of dipropylene glycol obtained by accelerated tests at various temperatures (40°, 50° and 70° C.). The solutions consisted of 20% DBNPA, 20% $H_2O$ and 60% dipropylene glycol (weight percent).

TABLE 1

Stability of DBNPA in aqueous solutions of dipropylene glycol at various temperatures.

| 40° C. | | | 50° C. | | | 70° C. | | |
|---|---|---|---|---|---|---|---|---|
| Time (days) | % DBNPA (w/w) | % Decomposition | Time (days) | % DBNPA (w/w) | % decomposition | Time (days) | % DBNPA (w/w) | % decomposition |
| 0 | 20.1 | 0 | 0 | 20.0 | 0 | 0 | 20.0 | 0 |
| 13 | 19.8 | 1.5 | 7 | 19.7 | 1.5 | 1 | 19.9 | 0.5 |
| 24 | 19.5 | 3.0 | 15 | 19.4 | 3.0 | 2 | 19.4 | 3.0 |
| 26 | 19.3 | 4.0 | 23 | 19.2 | 4.0 | 4.2 | 18.7 | 6.5 |
| 44 | 19.2 | 4.5 | 29 | 18.9 | 5.5 | | | |
| 56 | 19.1 | 5.0 | 35 | 18.5 | 7.5 | | | |
| 69 | 18.9 | 6.0 | 42 | 18.2 | 9.0 | | | |
| | | | 48 | 18.0 | 10.0 | | | |

From the Table it can be concluded that the rates of decomposition at the elevated temperatures, tested are completely satisfactory compared with the rates of decomposition of known formulations under similar conditions.

In the following Table 2 are presented the results concerning the stability of DBNPA in aqueous solutions of polypropylene glycol (MW 425), obtained in accelerated tests at 50° C. Experiment 2 presented in Table 2 does not illustrate the present invention and it is given only for comparison to show the high rate of decomposition which occurs when water is not present in the composition.

TABLE 2

Stability of DBNPA formulations at 50° C. with polypropylene glycol (425)

| Exp. No. | Compositions of formulations (% w/w) | | | Decomposition %/day |
|---|---|---|---|---|
| | % DBNPA | % water | % Solvent | |
| 1 | 20 | 10 | 70% polypropylene glycol (425) | 1.7 |
| 2 | 20 | 0 | 80% polypropylene glycol (425) | 11.5 |

In the following Table 3 are presented the rates of decomposition of DBNPA in propylene glycol solutions, determined at 50° C.

TABLE 3

Rate of decomposition of DBNPA in various formulations examined at 50° C.

| Composition of formulation (% w/w) | | | Rate of decomposition (%/day) |
|---|---|---|---|
| DBPNA | $H_2O$ | propylene glycol | |
| 20 | — | 80 | 1.4 |
| 20 | 5 | 75 | 0.23 |
| 20 | 10 | 70 | 0.20 |
| 20 | 20 | 60 | 0.17 |

The beneficial effect of water appears clearly by comparing the experiments in which the same solvent was utilized in the presence and absence of water, the absence of water causing over 6-fold increase in the decomposition. This supports the statement which appears in the U.K. Pat. No. 1,321,323 (on page 2, line 7) wherein it is mentioned that polypropylene glycol is unsuitable as a solvent in view of decomposition.

Using formulations of 20 parts DBNPA, 20 parts water and 60 parts dipropylene glycol (by weight) the rate of decomposition as a function of temperature was determined. The results obtained are presented in the following Table 4.

TABLE 4

Rate of decomposition of DBNPA in aqueous dipropylene glycol, as a function of temperature.

| Temperature (in °C.) | Rate of decomposition (in %/day) |
|---|---|
| 40 | 0.09 |
| 50 | 0.21 |
| 70 | 2.0 |

The above rates of decomposition indicate a completely satisfactory stability. Furthermore, a formulation containing 20 parts DBNPA, 20 parts water and 60 parts dipropylene glycol (all parts being by weight) was found to have lost no more than 5% of its activity over a period of one year at ambient temperature.

The following Tables 5 to 7 show additional experiments carried out to determine the decomposition of DBNPA solutions in various propylene glycols and water at various concentrations at ambient temperature. Tables 5 and 6 contain data collected at ambient temperature under decomposition conditions, deliberately accelerated to facilitate decomposition. This was achieved by storing relatively small samples of the test formulations in large, transparent or translucent bottles, thereby exposing the materials to considerable volumes of oxygen contained in the air of the head space. In addition, the bottles were placed near 40w fluorescent lamps. Such tests are designated as accelerated decomposition tests.

TABLE 5

Accelerated decomposition tests of dilute solutions of DBNPA in propylene glycol at ambient temperature.

| Exp. No. | Time days | DBNPA % w/w | Decompositions % |
|---|---|---|---|
| Solution Composition: 5% DBNPA - 20% $H_2O$ - 75% propylene glycol. | | | |
| 1 | 0 | 4.9 | 0 |
| 2 | 15 | 4.8 | 2.0 |
| 3 | 44 | 4.0 | 18.4 |
| Solution Composition: 10% DBNPA - 20% $H_2O$ - 70% propylene glycol. | | | |
| 4 | 0 | 9.6 | 0 |
| 5 | 15 | 9.2 | 4.2 |
| 6 | 44 | 8.8 | 8.3 |
| 7 | 60 | 7.6 | 20.8 |

TABLE 6

Accelerated decomposition tests of dilute solutions of DBNPA in polypropylene glycol "425" at ambient temperature.

| | Composition of Formulation | | | |
|---|---|---|---|---|
| Exp. No. | % DBNPA | % Water | % Polypropylene glycol 425 | Decomposition* %/day |
| 1 | 5 | 20 | 75 | 0.20 |
| 2 | 10 | 20 | 70 | 0.18 |

TABLE 7

Stability of DBNPA in aqueous solution of dipropylene glycol at ambient temperature.

| | Composition of Formulation | | | |
|---|---|---|---|---|
| Exp. No. | % DBNPA | % Water | % Dipropylene glycol | Decomposition %/day |
| 1 | 20 | 10 | 70 | 0.039 |
| 2 | 20 | 15 | 65 | 0.021 |
| 3 | 20 | 20 | 60 | 0.012 |
| 4 | 20 | 30 | 50 | 0.012 |
| 5 | 5 | 20 | 75 | 0.022 |
| 6 | 10 | 20 | 70 | 0.014 |
| 7 | 30 | 20 | 50 | 0.0018 |

*Decomposition rate based on composition after storage for 250 days.

Table 8 shows another experiment establishing the unexpected superiority of compositions to which water has been added as stabilizer. Experiments No. 1—4 of Table 8 are not part of the present invention.

TABLE 8

Stability of DBNPA in Dipropylene Glycol at Ambient Temperature

| | Composition of formulations (w/w) | | | |
|---|---|---|---|---|
| Exp. No. | % $H_2O$ | % DBNPA | % Dipropylene Glycol | Decomposition* % day |
| 1 | 0 | 5 | 95 | 0.07 |
| 2 | 0 | 10 | 90 | 0.06 |
| 3 | 0 | 20 | 80 | 0.03 |
| 4 | 20 | 20 | 60 | 0.01 |

*Decomposition rate based on composition after storage for 200 days.

The rate of decomposition of the DBNPA was determined in the above Tables by measuring the relative DBNPA content of the various antimicrobial compositions using an iodometry test. In such test method, an excess of potassium iodine is added to the antimicrobial composition and the amount of elemental iodine which has been liberated from the potassium iodide—by the oxidation of potassium iodide with the DBNPA—is determined by titration with a standard solution of sodium thiosulfate. The amount of DBNPA present in the composition tested is subsequently calculated on the basis of the amount of elemental iodine liberated thereby.

One of the requirements for the antimicrobial compositions is the freeze-thaw behavior of the formulations. Tests consisting of seven temperature cycles (each conducted for 24 hours), show that such compositions have excellent freeze-thaw stability. The test was carried out as follows: The sample was first kept at −15° C. followed by thawing intervals to ambient temperature. The results established that the formulation did not freeze or produce precipitate or fractionate during these cycles.

The compositions according to the present invention are clear, substantially colorless and stable for extended periods under a wide variety of storage, packaging and handling conditions. They are easily handled and can be employed directly as antimicrobial agents or diluted with conventional inert diluents or substrates, such as water or other solvents known in the prior art, such as polyalkylene glycols, to prepare ultimate treating compositions for application to bacteria and fungi. They can be mixed with a wide variety of aqueous solutions and dispersions subject to microbial attack in amounts sufficient to provide an antimicrobial amount of the DBNPA in the dispersion. In particular for antimictobial use in most applications, ultimate concentrations of DBNPA from 0.5 to 500 part per million were found to be useful.

The compositions according to the present invention can be employed for many purposes, such as in preserving water, industrial wash water or paper pulp slurries having a neutral or acid pH. In addition to the above uses, the compositions according to the present invention can be employed in the preservation of oil-water emulsions, without adversely affecting the physical and chemical properties of the emulsion.

In addition to the beneficial effect imparted to the stability of the compositions, the inclusion of water in the formulation reduces the cost of the latter and also decreases the overall costs in the production of the DBNPA itself. As known, in some methods for the manufacture of DBNPA, a wet product containing about 5–10% water is obtained after filtration and a careful drying operation is necessary to obtain the dry product. Since DBNPA is corrosive and less stable at elevated temperatures, such drying operations are preferably to be avoided. However, since the presence of water in the claimed formulations is not only acceptable but actually beneficial, the drying operation is not necessary.

The microbiological activity of the compositions according to the present invention was tested with liquors obtained from actual streams from the plant of a commercial paper mill. Microorganisms were isolated from such solutions and tested at levels of $10^6$ microorganisms/ml of solution, using 100 ppm of a composition containing 20 parts DBNPA, 20 parts water and 60 parts dipropylene glycol (all parts being by weight). The results obtained, as examined by the Institute of Food Microbiology, Tirat Hacarmel (Israel), are presented in the following Table 9.

TABLE 9

Microbiological activity of a formulation (100 ppm) containing 20 parts DBNPA, 20 parts water and 60 parts dipropylene glycol with paper mill liquors.

| Microorganisms (M. O.) isolated from alkaline streams (M. O./ml). | | Microorganisms (M. O.) isolated from acid streams (in M. O./ml) | | |
|---|---|---|---|---|
| Initial solution | After 3 hours at pH 7 | Initial solution | After 3 h at pH 4.5 | After 3 h at pH 7 |
| $2.5 \times 10^6$ | less than 10 | $1.2 \times 10^6$ and $2.2 \times 10^6$ | 100 | 40, 50 |

Blank tests run with dipropylene glycol without DBNPA retained the same concentration of M.O/ml as the initial solution.

The following conclusions can be drawn from the results presented in the above Table 9:

Dipropylene glycol itself has no effect on the microorganisms.

In the case of microorganisms isolated from the neutral stream, examined at pH 7 (which is the pH of the actual stream), the formulations reduced the number of microorganisms/ml from $2.5 \times 10^6$ to less than 10.

Microorganisms from the acid stream were examined both at pH 4.5 (pH of actual stream) and at pH 7. The number of microorganisms per ml dropped from $1.2 \times 10^6$–$2.2 \times 10^6$ to form 10 to 100 (from a statistical interpretation, this spread of values is considered insignificant).

While the present invention has been described with specific embodiments thereof, it will be understood that it is capable of further modifications, and this patent is intended to cover any variation, uses or adaptations of the invention and including such departures from the present disclosure as come within known and customary practice in the art to which the invention pertains and as may be applied to the essential features hereinbefore set forth and as fall within the scope of the invention.

What is claimed is:

1. A stable antimicrobial liquid concentrate composition, consisting essentially of a solution of 1—30% by weight of dibromonitrilopropionamide (DBNPA) in propylene glycol, and a stabilizing amount of water, said stabilizing amount of water being 5—30% by weight.

2. A composition in accordance with claim 1, wherein said propylene glycol is selected from the group consisting of monopropylene glycol, dipropylene glycol, polypropylene glycol and mixtures thereof.

3. A composition in accordance with claim 1, wherein said propylene glycol comprises dipropylene glycol and the composition contains about 20% by weight DBNPA, about 20% by weight water, and about 60% by weight dipropylene glycol.

4. A method for inhibiting microbial growth in an aqueous fluid solution or dispersion, comprising admixing a concentrate composition according to claim 1, with the fluid in an amount sufficient to provide an antimicrobial concentration of dibromonitrilopropionamide in the fluid.

5. The method of claim 4, wherein the concentrate composition is administered in an amount sufficient to provide a concentration of from 0.5 to 500 ppm dibromonitrilopropionamide in the fluid.

6. The method of claim 4, wherein the concentrate composition is diluted before admixture with the fluid.

7. The method of claim 6, wherein the concentrate composition is diluted with a solvent.

8. The method of claim 6, wherein the concentrate composition is diluted with water.

9. The method of claim 8, wherein the solvent is a polypropylene glycol.

10. The method of claim 4, wherein the aqueous fluid is an industrial wash water or a paper pulp slurry having a neutral or acid pH.

* * * * *